(12) United States Patent
Zhou et al.

(10) Patent No.: US 12,594,247 B2
(45) Date of Patent: Apr. 7, 2026

(54) EDGED CATAPLASM AND MANUFACTURING PROCESS

(71) Applicant: Planet (Anhui) Pharmaceutical Co., Ltd., Chuzhou (CN)

(72) Inventors: Xiaoshen Zhou, Chuzhou (CN); Yunqiang Ying, Chuzhou (CN); Yuan Zhu, Chuzhou (CN)

(73) Assignee: Planet (Anhui) Pharmaceutical Co., Ltd., Chuzhou (CN)

( * ) Notice: Subject to any disclaimer, the term of this patent is extended or adjusted under 35 U.S.C. 154(b) by 205 days.

(21) Appl. No.: 18/106,501

(22) Filed: Feb. 7, 2023

(65) Prior Publication Data

US 2024/0173268 A1 May 30, 2024

(30) Foreign Application Priority Data

Nov. 24, 2022 (CN) .......................... 202211484907.0

(51) Int. Cl.
*A61K 9/70* (2006.01)
*A61F 13/00* (2024.01)
(Continued)

(52) U.S. Cl.
CPC ................ *A61K 9/70* (2013.01); *A61K 47/02* (2013.01); *A61K 47/32* (2013.01); *A61K 47/34* (2013.01)

(58) Field of Classification Search
None
See application file for complete search history.

(56) References Cited

U.S. PATENT DOCUMENTS

| | | | | |
|---|---|---|---|---|
| 2012/0238932 | A1* | 9/2012 | Atteia | ................ A61F 13/0276 |
| | | | | 156/247 |
| 2013/0089599 | A1* | 4/2013 | DeSilva | .............. A61K 9/1647 |
| | | | | 424/490 |
| 2022/0087948 | A1* | 3/2022 | Murphy | .............. A61K 36/185 |

FOREIGN PATENT DOCUMENTS

| | | | | |
|---|---|---|---|---|
| CN | 206548699 | U | * | 10/2017 |
| CN | 213789152 | U | * | 7/2021 |

(Continued)

OTHER PUBLICATIONS

Stanizzi, A., Bottoni, M., Torresetti, M., Campanati, A., & Di Benedetto, G. (2014). Topical use of a-tocopherol acetate in delayed wound healing. International Wound Journal, 12(6), 746. (Year: 2014).*

(Continued)

*Primary Examiner* — Kyung S Chang
(74) *Attorney, Agent, or Firm* — Bayramoglu Law Offices

(57) ABSTRACT

An edged cataplasm and a manufacturing process are disclosed. The edged cataplasm includes a support layer; a drug layer, which adheres to the bottom of the support layer; a cross-type release film, which adheres to the bottom of the drug layer. The cross-type release film includes a first-release film piece and a second-release film piece, and the adjacent edges of the first-release film piece and the second-release film piece are partially overlapped. In addition, the edged cataplasm further includes a waterproof-breathable adhesive layer, which adheres to the top of the support layer and coated with silver ions or a nano antibiotic layer; a polyethylene terephthalate (PET) film, which adheres to the top of the waterproof-breathable adhesive layer. The PET film includes a first part and a second part, and the adjacent edges of the first part and the second part are arranged as an aligned S-shaped edge.

2 Claims, 5 Drawing Sheets

(51) Int. Cl.
| | |
|---|---|
| *A61F 13/02* | (2024.01) |
| *A61F 13/0246* | (2024.01) |
| *A61K 47/02* | (2006.01) |
| *A61K 47/32* | (2006.01) |
| *A61K 47/34* | (2017.01) |
| *A61L 15/44* | (2006.01) |
| *A61L 15/58* | (2006.01) |

(56) References Cited

FOREIGN PATENT DOCUMENTS

| | | | | | |
|---|---|---|---|---|---|
| GB | 2369997 A | * | 6/2002 | ....... | A61F 13/00063 |
| WO | WO-2010106571 A2 | * | 9/2010 | ............ | A61K 31/20 |

OTHER PUBLICATIONS

Description CN206548699U. Lu Kang Jan. 22, 2025. Retrieved from the internet: <https://translationportal.epo.org/emtp/translate/?ACTION=description-retrieval&COUNTRY=CN&ENGINE=google&FORMAT=docdb&KIND=U&LOCALE=en_EP&NUMBER=206548699&SRCLANG=zh&TRGLANG=en>. (Year: 2024).*
Zhou et al. Jul. 27, 2021. Description CN213789152U Translation. <https://translationportal.epo.org/emtp/translate/?ACTION=description-retrieval&COUNTRY=CN&ENGINE=google&FORMAT=docdb&KIND=U&LOCALE=en_EP&NUMBER=213789152&SRCLANG=zh&TRGLANG=en> (Year: 2021).*

* cited by examiner

S-shaped opening

Front

Back

A-A'' cross-section

B-B' cross-section

C-C' cross-section

D-D' cross-section

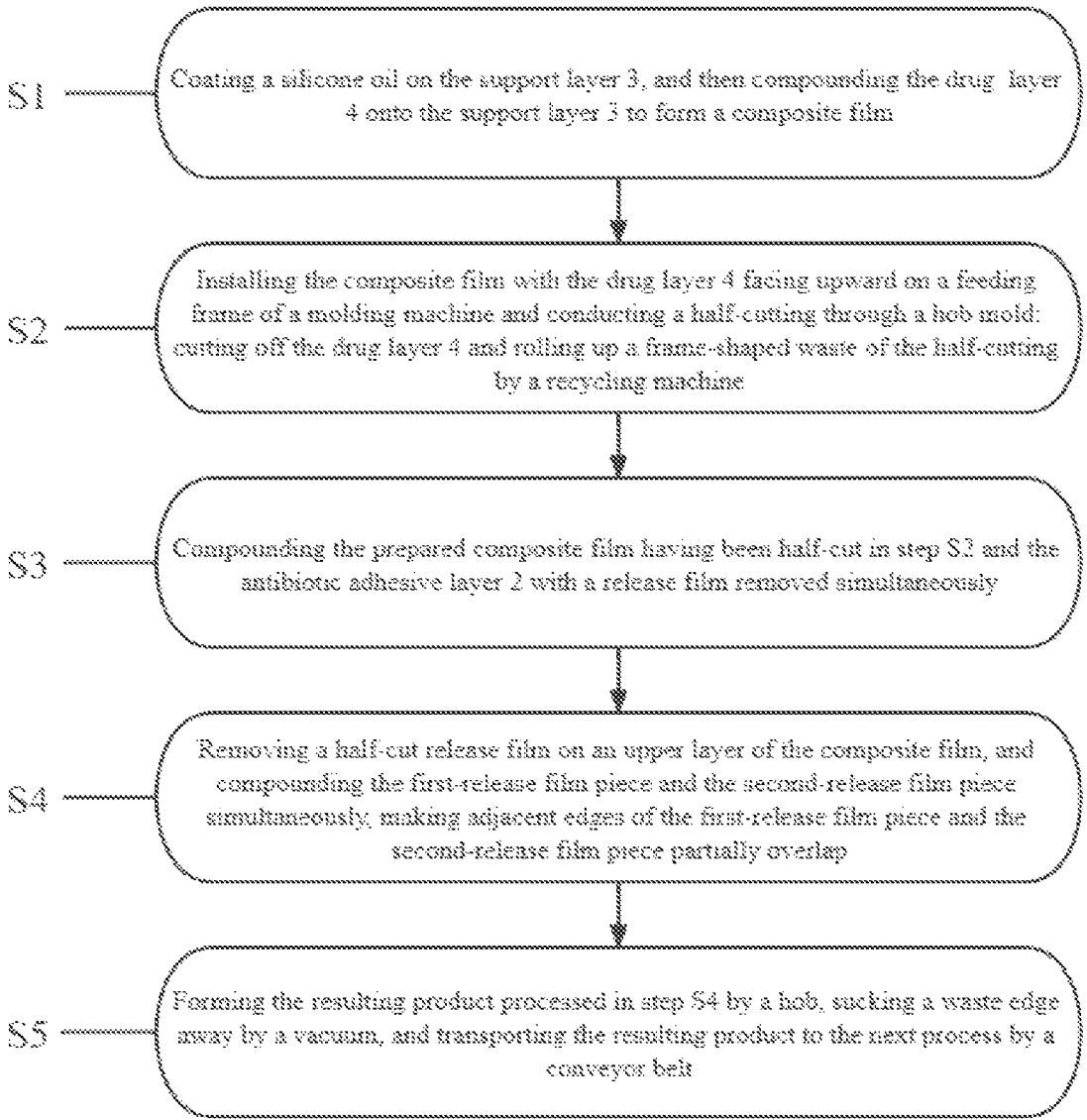

S1 —— Coating a silicone oil on the support layer 3, and then compounding the drug layer 4 onto the support layer 3 to form a composite film S2 —— Installing the composite film with the drug layer 4 facing upward on a feeding frame of a molding machine and conducting a half-cutting through a hob mold; cutting off the drug layer 4 and rolling up a frame-shaped waste of the half-cutting by a recycling machine S3 —— Compounding the prepared composite film having been half-cut in step S3 and the antibiotic adhesive layer 2 with a release film removed simultaneously S4 —— Removing a half-cut release film on an upper layer of the composite film, and compounding the first-release film piece and the second-release film piece simultaneously, making adjacent edges of the first-release film piece and the second-release film piece partially overlap S5 —— Forming the resulting product processed in step S4 by a hob, sucking a waste edge away by a vacuum, and transporting the resulting product to the next process by a conveyor belt

FIG. 8

EDGED CATAPLASM AND MANUFACTURING PROCESS

CROSS REFERENCE TO THE RELATED APPLICATIONS

This application is based upon and claims priority to Chinese Patent Application No. 202211484907.0, filed on Nov. 24, 2022, the entire contents of which are incorporated herein by reference

TECHNICAL FIELD

The present disclosure belongs to the technical field of cataplasms and relates to an edged cataplasm and a manufacturing process.

BACKGROUND

The shape of the traditional cataplasm is rectangular, and the cataplasm has a three-layer structure:

① a base made of non-woven fabric and other materials,
② a drug-containing hydrogel, and
③ a release film.

The surface of the non-woven fabric is coated with the drug-containing hydrogel having a certain viscosity, and the upper layer of the hydrogel is covered with the release film. The release film is torn before using the cataplasm, and the surface of the non-woven fabric coated with the drug-containing hydrogel is stuck on the skin.

The traditional cataplasm falls off easily after being stuck due to the twisting of body joints and clothes rubbing against the cataplasm. Moreover, the traditional cataplasm is not waterproof, so it falls off easily after bathing. Additionally, the traditional cataplasm has great limitations and problems in the sticking position and the application.

SUMMARY

To solve the problems of the prior art cataplasm, the present disclosure provides an edged cataplasm and a manufacturing process.

The technical solution adopted by the present disclosure to solve the technical problem is as follows:

an edged cataplasm, including:

a support layer;

a drug layer, which adheres to the bottom of the support layer, and the drug layer is a drug-containing hydrogel;

a cross-type release film, which adheres to the bottom of the drug layer. The cross-type release film includes a first-release film piece and a second-release film piece. The first-release film piece and the second-release film piece adhere to both sides of the drug layer respectively, and the adjacent edges of the first-release film piece and the second-release film piece are partially overlapped;

a waterproof-breathable adhesive layer arranged on the top of the support layer; and an antibiotic layer sandwiched between the waterproof-breathable adhesive layer and the support layer.

The corners of the antibiotic layer, the support layer, the drug layer, the cross-type release film, and the waterproof-breathable adhesive layer are rounded.

The lengths and widths of each of the antibiotic layer, the support layer, and the drug layer are less than the lengths and widths of each of the cross-type release film and the waterproof-breathable adhesive layer. The waterproof-breathable adhesive layer, and the cross-type release film are bonded and adhered at an edge around the edged cataplasm.

Preferably, the edged cataplasm further includes a polyethylene terephthalate (PET) film. The PET film adheres to the top of the waterproof-breathable adhesive layer and includes a first part and a second part. The first part and the second part adhere to both sides of the waterproof-breathable adhesive layer, respectively, and the adjacent edges of the first part and the second part are arranged as an aligned S-shaped edge.

Preferably, in the edged cataplasm of the present disclosure, the support layer is a polyethylene (PE) mesh film, a non-woven fabric, a woven fabric, or a scrim Preferably, in the edged cataplasm of the present disclosure, the main body of the waterproof-breathable adhesive layer is a polyurethane (PU) film having a waterproof-breathable property and an adhesive property.

Preferably, in the edged cataplasm of the present disclosure, the drug-containing hydrogel is added a vitamin E acetate having antioxidant and anti-free radical properties.

A manufacturing process for an edged cataplasm for preparing the edged cataplasm described above includes:

S1, coating a silicone oil on the support layer and then compounding the drug layer onto the support layer to form a composite film.

Preferably, the manufacturing process for the edged cataplasm of the present disclosure further includes:

S2, installing the composite film with the drug layer facing upward on a feeding frame of a molding machine and conducting a half-cutting through a hob mold: cutting off the drug layer and rolling up a frame-shaped waste of the half-cutting by a recycling machine.

Preferably, the manufacturing process for the edged cataplasm of the present disclosure further includes:

S3, compounding the prepared composite film having been half-cut in step S2 and the waterproof-breathable adhesive layer with a release film removed, simultaneously.

Preferably, the manufacturing process for the edged cataplasm of the present disclosure further includes:

S4, removing a half-cut release film on the upper layer of the prepared composite film and compounding a first-release film piece and a second-release film piece simultaneously to make the adjacent edges of the first-release film piece and the second-release film piece partially overlap.

Preferably, the manufacturing process for the edged cataplasm of the present disclosure further includes:

S5, forming the resulting product processed in step S4 by a hob, sucking a waste edge away by a vacuum, and transporting the resulting product to the next process by a conveyor belt.

Preferably, in the manufacturing process for the edged cataplasm of the present disclosure, in step S3, one surface of the waterproof-breathable adhesive layer adheres to the release film, and the other surface adheres to the PET film.

The advantages of the present disclosure are as follows:

The novel cataplasm of the present disclosure solves the problems of the traditional cataplasm that easily falls off the skin and is not waterproof and can be applied to various body joints, thereby broadening the application of the product.

BRIEF DESCRIPTION OF THE DRAWINGS

The technical solution of the present disclosure is further explained in combination with the attached drawings and embodiments.

FIG. 8 is a flow chart showing a manufacturing process of the edged cataplasm of the embodiment of the present disclosure.

Figures 1, 2:
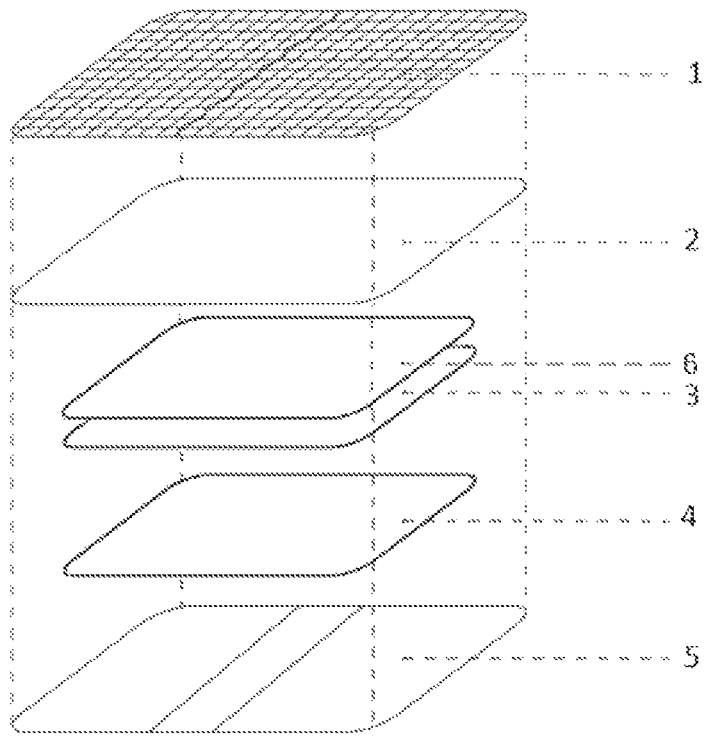
FIG. 1 is a schematic diagram showing an exploded structure of an edged cataplasm of an embodiment of the present disclosure.
FIG. 2 is a schematic diagram showing a front structure of the edged cataplasm of the embodiment of the present disclosure.

The reference numerals of the attached drawings are as follows:

PET film 1; waterproof-breathable adhesive layer 2; support layer 3; drug layer 4; cross-type release film 5; antibiotic layer 6.

DETAILED DESCRIPTION OF THE EMBODIMENTS

It should be noted that the embodiments and the features in the embodiments of the present disclosure may be combined if there is no conflict.

In the description of the present disclosure, it is understood that the terms "center", "longitudinal", "transverse", "up", "down", "front", "back", "left", "right", "vertical", "horizontal", "top", "bottom", "inside", "outside", etc., indicating a location or position relationship are based on the location or position relationship shown in the attached drawings. These terms are used only for the convenience of describing and simplifying the description of the present disclosure and are not to indicate or imply that the device or element must have a particular orientation and be manufactured and operated in a particular orientation. Therefore, these terms shall not be construed as a limitation on the scope of protection of the present disclosure. Furthermore, the terms "first", "second", etc., are used only for descriptive purposes and are not to be understood as indicating or implying relative importance or the quantity of the technical features. Thus, a feature defined as "first", "second", etc., may explicitly or implicitly include one or more of these features. In the description of the present disclosure, "multiple" means two or more unless otherwise noted.

In the description of the present disclosure, it is noted that the terms "installation", "connection", and "connected" shall be given the broadest interpretation unless otherwise expressly specified and defined. For example, the connection may be fixedly connected, detachably connected, or integrally connected; it may be mechanically connected or electrically connected; and it may be directly connected, indirectly connected through an intermediary, or communicated by two components. For those who have ordinary skills in the art, the specific meaning of the above terms in the present disclosure should be understood by the specific circumstances. If X, Y, and Z directions or X, Y, and Z axes are involved in the embodiments, they are all based on the Cartesian coordinate system.

The technical solution of the present disclosure is explained in combination with the attached drawings and embodiments.

Embodiment

Figure 3:
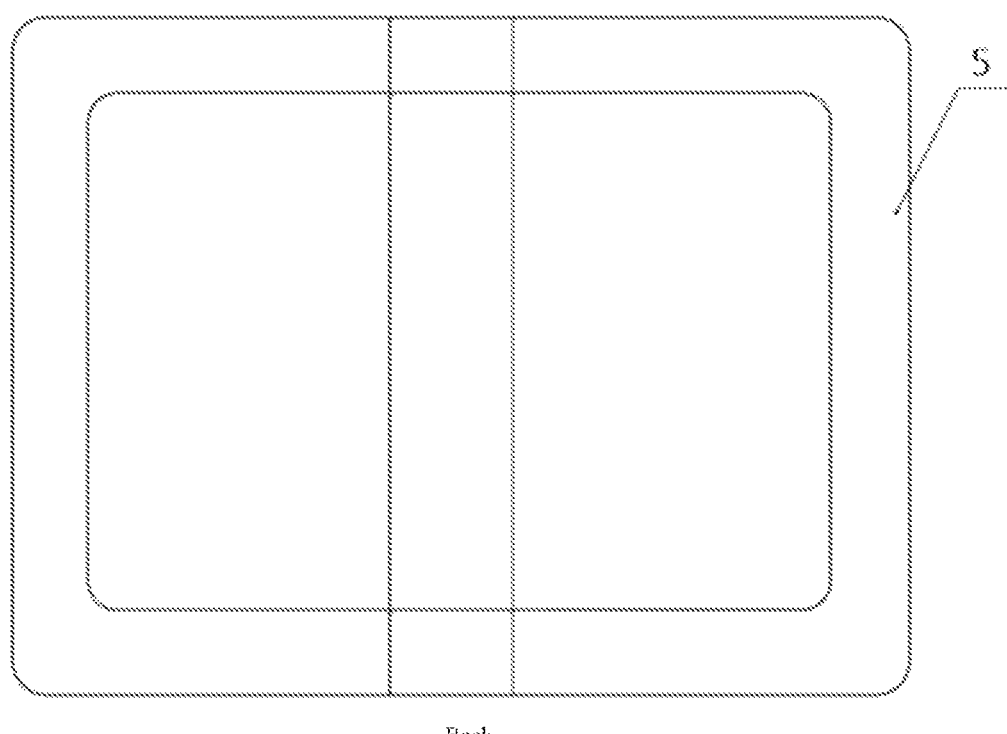
FIG. 3 is a schematic diagram showing a back structure of the edged cataplasm of the embodiment of the present disclosure.
Figure 4:
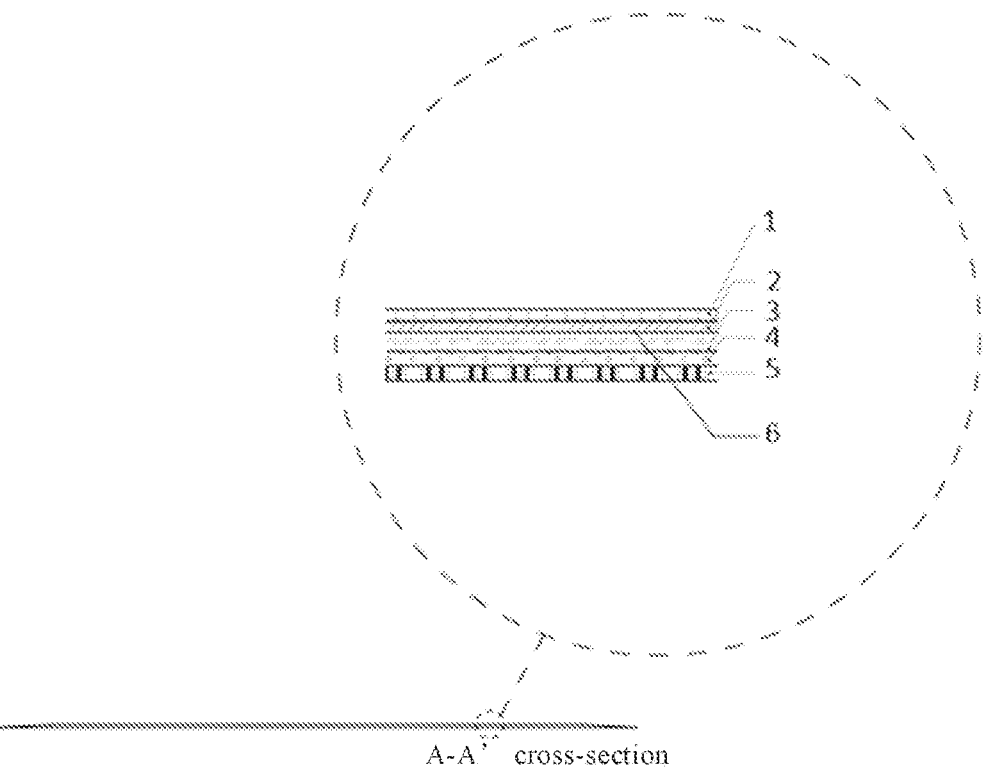
FIG. 4 is a schematic diagram showing a A-A' cross-section of FIG. 2.
Figure 5:
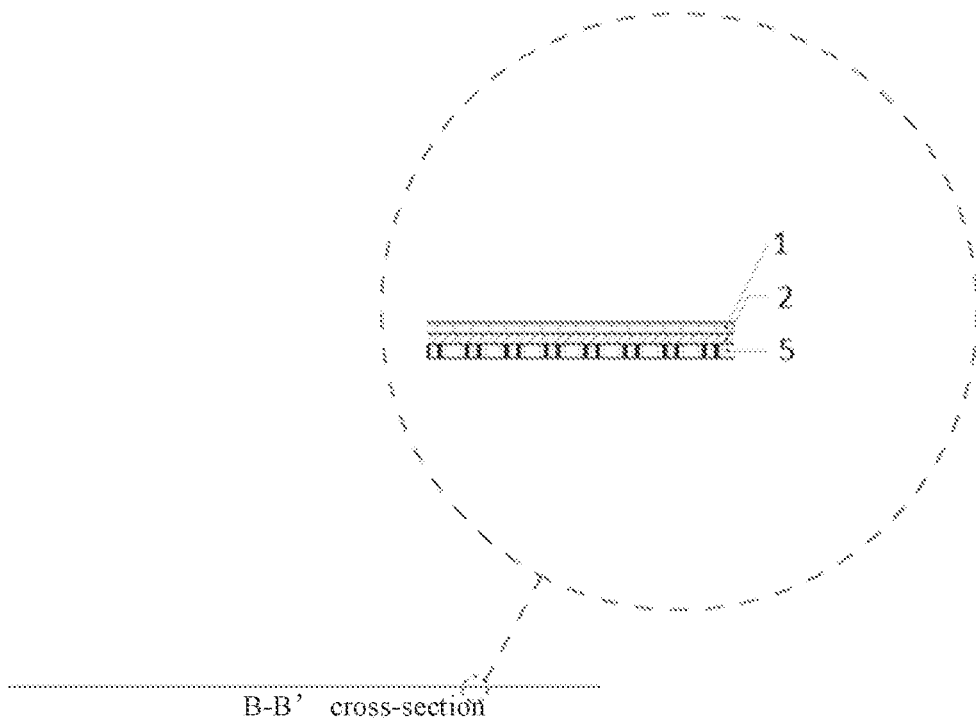
FIG. 5 is a schematic diagram showing a B-B' cross-section of FIG. 2.
Figure 6:
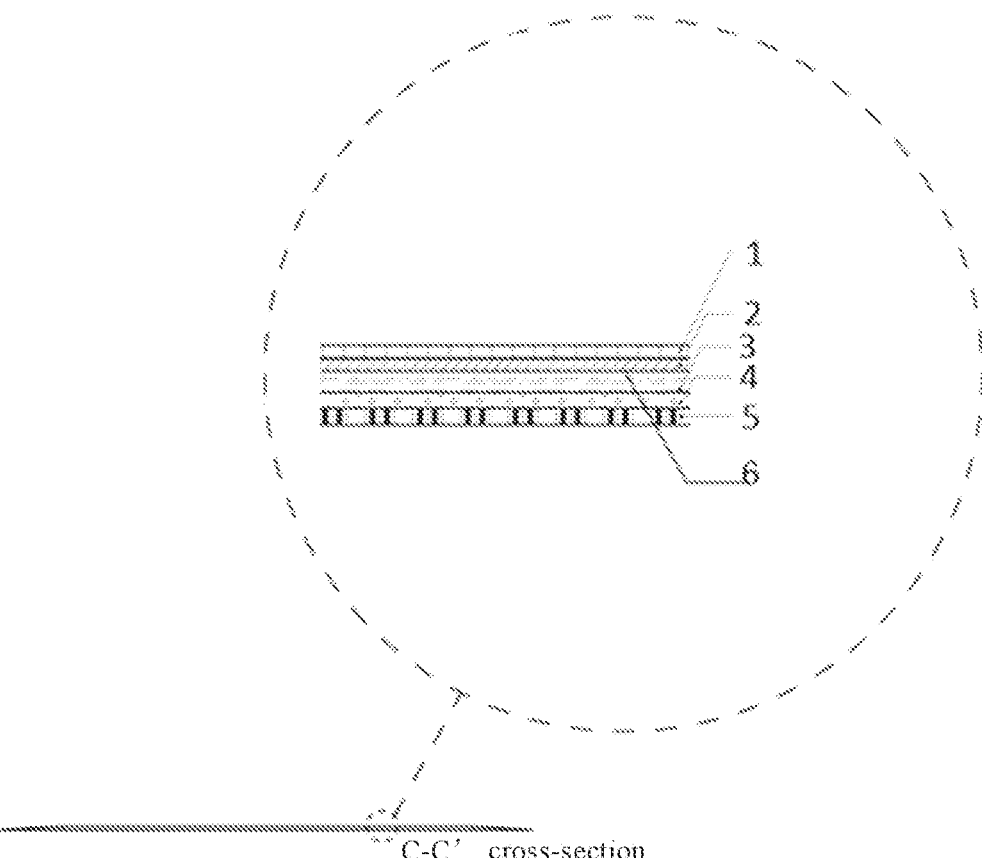
FIG. 6 is a schematic diagram showing a C-C' cross-section of FIG. 2.
Figure 7:
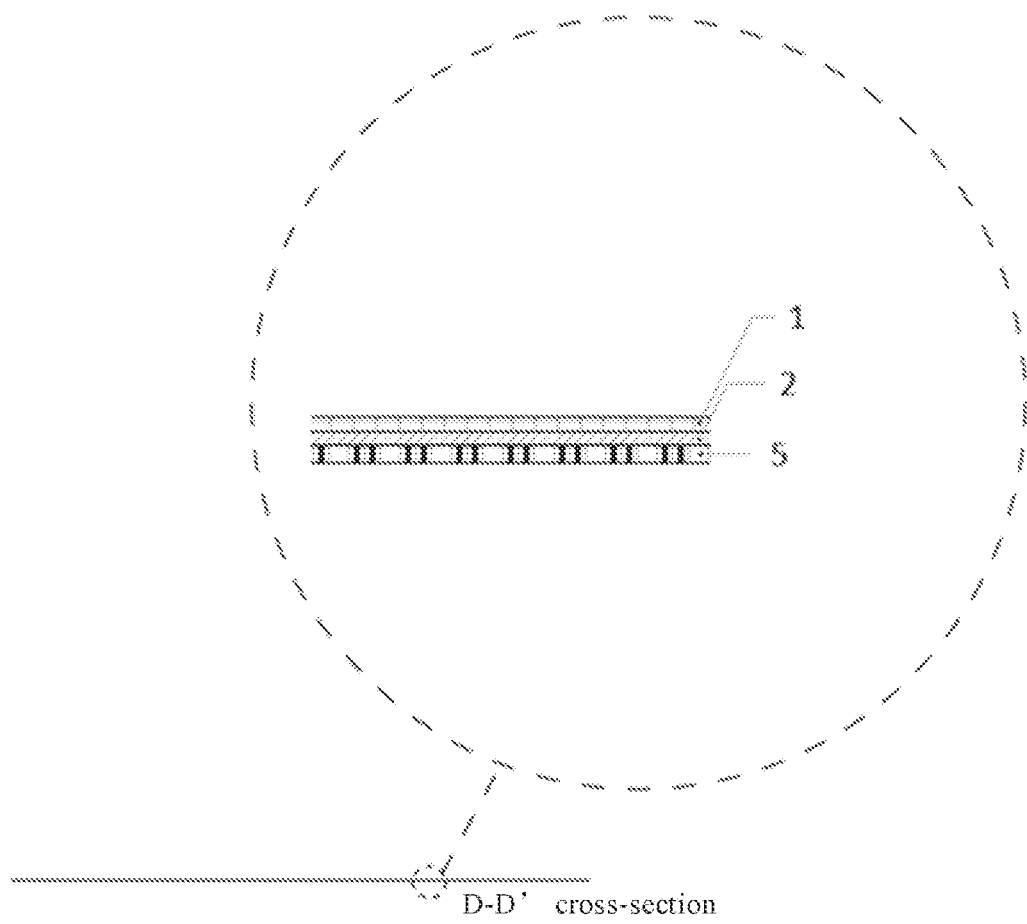
FIG. 7 is a schematic diagram showing a D-D' cross-section of FIG. 2.

As shown in FIGS. 1-7, the embodiment provides an edged cataplasm, which includes:

a support layer 3;

a drug layer 4, which adheres to the bottom of the support layer 3 is a drug-containing hydrogel;

a cross-type release film 5, which adheres to the bottom of the drug layer 4. The cross-type release film 5 includes a first-release film piece and a second-release film piece. The first-release film piece and the second-release film piece adhere to both sides of the drug layer 4, respectively, and the adjacent edges of the first-release film piece and the second-release film piece are partially overlapped. The structure of the cross-type release film 5 is convenient for the user to tear off;

a waterproof-breathable adhesive layer 2 arranged on the top of the support layer 3; an antibiotic layer 6 sandwiched between the waterproof-breathable adhesive layer 2 and the support layer 3. The drug-containing hydrogel of the drug layer 4 absorbs the wound tissue fluid to form a moist healing environment, and the liquid is allowed to penetrate into the support layer 3, the antibiotic layer 6, and the waterproof-breathable adhesive layer 2 to communicate the upper and lower structures;

a PET film 1, which adheres to the top of the waterproof-breathable adhesive layer 2 and includes a first part and a second part. The first part and the second part adhere to both sides of the waterproof-breathable adhesive layer 2, respectively, and the adjacent edges of the first part and the second part are arranged as aligned S-shaped edges.

The corners of the antibiotic layer 6, the support layer 3, the drug layer 4, the cross-type release film 5, the waterproof-breathable adhesive layer 2, and the PET film 1 are rounded, which are designed to greatly reduce the warping or falling off caused by the user's clothing rubbing against the cataplasm.

As shown in FIGS. 1-7, in the edged cataplasm of the embodiment, the length and width of the support layer 3, the antibiotic layer 6, and the drug layer 4 are designed to be less than the length and width of the cross-type release film 5, the waterproof-breathable adhesive layer 2, and the PET film 1, so that the PET film 1, the waterproof-breathable adhesive layer 2, and the cross-type release film 5 are bonded and adhered at the edge around the edged cataplasm. Support layer 3, the antibiotic layer 6, and the drug layer 4 internal are enclosed and protected within the cataplasm. In this way, the efficacy of the support layer 3 and the drug layer 4 is ensured, and the S-shaped edge of PET film 1 allows for easy removal.

Preferably, in the edged cataplasm of the embodiment, the support layer 3 is polyethylene (PE) mesh film, non-woven fabric, woven fabric, or scrim.

Preferably, in the edged cataplasm of the embodiment, the main body of the waterproof-breathable adhesive layer 2 is a polyurethane (PU) film having a waterproof-breathable property and an adhesive property. The PU film is coated with silver ions or a nano antibiotic layer.

Preferably, in the edged cataplasm of the embodiment, the addition of vitamin E acetate, which has antioxidant and anti-free radical properties, to the hydrogel preparation in the embodiment has a good effect on reducing the irritation of the hydrogel paste on the skin, moisturizing the skin, and protecting the skin and can also effectively solve the problem that the polymer material in the hydrogel preparation easily turns yellow when exposed to heat. At the same time, the vitamin E acetate also has a certain auxiliary function for the transdermal absorption of the active ingredients in the preparation.

The embodiment provides a manufacturing process for an edged cataplasm for preparing the edged cataplasm described above. As shown in FIG. 8, the steps include:

S1, the support layer 3 is coated with the silicone oil, and then the drug layer 4 is compounded onto the support layer 3 to form a composite film.

S2, the composite film with the drug layer 4 facing upward, is installed on a feeding frame of a molding machine and is half-cut through a hob mold: the drug layer 4 is cut off, and a frame-shaped waste of the half-cutting is rolled up by a recycling machine.

S3, the prepared composite film having been half-cut in step S2 and the waterproof-breathable adhesive layer 2 with a release film removed are compounded, simultaneously.

S4, a half-cut release film on the upper layer of the prepared composite film is removed, and the first-release film piece and the second-release film piece are compounded simultaneously to make the adjacent edges of the first-release film piece and the second-release film piece partially overlap.

S5, the resulting product processed in step S4 is formed by a hob, the waste edge is sucked away by a vacuum, and the resulting product is transported to the next process by a conveyor belt.

Preferably, in step S3 of the manufacturing process for the edged cataplasm:

one surface of the waterproof-breathable adhesive layer 2 adheres to a release film, and the other surface adheres to the PET film 1.

Embodiment 2

In this embodiment, in order to simplify production and control costs, the PET film 1 in Embodiment 1 is removed and the waterproof-breathable adhesive layer 2 is adaptively thickened.

The above-preferred embodiments of the present disclosure are examples. One of ordinary skill in the art can make various changes and modifications within the scope of the present disclosure without departing from the technical ideas of the present disclosure. The technical scope of the present disclosure is not limited to the contents of the specification and must be determined according to the scope of the claims.

What is claimed is:

1. An edged cataplasm, comprising the following layers arranged sequentially from top to bottom:

a polyethylene terephthalate (PET) film comprising a first part and a second part, a waterproof-breathable adhesive layer, an antibiotic layer, a support layer, a drug layer, and a release film; wherein the PET film adheres to the top of the waterproof-breathable adhesive layer;

the waterproof-breathable adhesive layer is a polyurethane (PU) film having a waterproof-breathable property and an adhesive property;

the antibiotic layer comprises silver ions or a nano antibiotic;

the support layer is a polyethylene (PE) mesh film;

silicone oil is coated on the support layer and the drug layer is compounded onto the support layer to form a composite film, and the drug layer is a drug-containing hydrogel, wherein the drug-containing hydrogel contains a vitamin E acetate having antioxidant and anti-free radical properties;

the release film adheres to the bottom of the drug layer and comprises a first-release film piece and a second-release film piece; the first-release film piece and the second-release film piece adhere to the drug layer, and adjacent edges of the first-release film piece and the second-release film piece are partially overlapped; and wherein the antibiotic layer, the support layer, the drug layer, the release film, and the waterproof-breathable adhesive layer are rounded;

each layer has sides with a length and a width and the length and the width of each of the antibiotic layer, the support layer, and the drug layer are less than the length and the width of each of the release film and the waterproof-breathable adhesive layer; and the waterproof-breathable adhesive layer, and the release film are bonded and adhered at an edge around the edged cataplasm.

2. The edged cataplasm according to claim 1, wherein a first part and a second part of the PET film adhere to both sides of the waterproof-breathable adhesive layer respectively, and adjacent edges of the first part and the second part are arranged as an aligned S-shaped edge.

* * * * *